United States Patent
El-Hashim et al.

(10) Patent No.: US 9,238,019 B2
(45) Date of Patent: Jan. 19, 2016

(54) ANTITUSSIVE AND BRONCHODILATOR USES FOR ENAMINONE ESTER

(75) Inventors: Ahmed Z. El-Hashim, Safat (KW); Ivan O. Edafiogho, Safat (KW); Samuel B. Kombian, Safat (KW); Mariam H. Yousif, Safat (KW)

(73) Assignee: UNIVERSITY OF KUWAIT, Safat (KW)

( * ) Notice: Subject to any disclaimer, the term of this patent is extended or adjusted under 35 U.S.C. 154(b) by 1032 days.

(21) Appl. No.: 12/662,364

(22) Filed: Apr. 13, 2010

(65) Prior Publication Data

US 2010/0204321 A1 Aug. 12, 2010

Related U.S. Application Data

(63) Continuation-in-part of application No. 11/307,003, filed on Jan. 18, 2006, now abandoned.

(51) Int. Cl.
*A61K 31/24* (2006.01)
*A61K 9/00* (2006.01)

(52) U.S. Cl.
CPC .............. *A61K 31/24* (2013.01); *A61K 9/0019* (2013.01); *A61K 9/0073* (2013.01)

(58) Field of Classification Search
CPC .... A61K 31/24; A61K 9/0019; A61K 9/0073
USPC ................ 514/751, 743, 675, 676; 560/1
See application file for complete search history.

(56) References Cited

U.S. PATENT DOCUMENTS

| 5,468,775 A | 11/1995 | Scott et al. |
| 5,616,615 A | 4/1997 | Scott et al. |
| 7,820,663 B2 * | 10/2010 | Hogenkamp et al. ......... 514/247 |

FOREIGN PATENT DOCUMENTS

WO   WO 93/17678   9/1993

OTHER PUBLICATIONS

Remington, The Science and Practice of Pharmacy, Nineteenth Edition-1995.*

* cited by examiner

*Primary Examiner* — Shobha Kantamneni
(74) *Attorney, Agent, or Firm* — Richard C. Litman

(57) ABSTRACT

The antitussive and bronchodilator use for an enaminone ester relates to the use of ethyl 4-[(4-chlorophenyl)amino]-6-methyl-2-oxocyclohex-3-en-1-oate (also referred to as "enaminone E121") for treatment of respiratory conditions, and particularly to use of the ester as the active ingredient in a cough suppressant for nonproductive cough. The ester may be used to achieve an antitussive effect, a bronchodilator effect, or both in a patient in need thereof. The ester may be formulated in any desired delivery form (such as a tablet, a capsule, a time-release capsule, a syrup, a liquid, an injection, a spray, or an inhalant), and be combined with any suitable pharmaceutical carrier, vehicles, binders, fillers, disintegrators, lubricants, solubilizers, emulsifiers, surfactants, and other excipients.

14 Claims, 4 Drawing Sheets

US 9,238,019 B2

ANTITUSSIVE AND BRONCHODILATOR USES FOR ENAMINONE ESTER

CROSS-REFERENCE TO RELATED APPLICATION

This application is a continuation-in-part of U.S. patent application Ser. No. 11/307,003, filed on Jan. 18, 2006 now abandoned.

BACKGROUND OF THE INVENTION

1. Field of the Invention

The present invention relates to cough suppressants and to treatments for respiratory conditions, and particularly to antitussive and bronchodilator use for an enaminone ester, viz., ethyl 4-[(4-chlorophenyl)amino]-6-methyl-2-oxocyclohex-3-en-1-oate.

2. Description of the Related Art

Coughs, particularly chronic coughs, are a very common clinical problem with a high prevalence rate. Unfortunately, current over-the-counter drugs provide very little therapeutic benefit and often have serious side effects. Due to a lack of treatment alternatives, these drugs still remain among the most widely used drugs. There is evidence to show that some types of coughs, such as the nonproductive chronic cough associated with smoking, seems to improve following administration of $\beta_2$ agonists, which suggests that this type of cough is bronchodilator sensitive. Additionally, patients with a nonproductive cough associated with airflow obstruction seem to derive improvement in their cough following $\beta_2$ agonist treatment.

Treatment with a combination of the antitussive agent dextromethorphan and salbutamol (salbutamol is the International Nonproprietary Name; albuterol is the U.S. Adopted Name) has been reported to be more effective in reducing citric acid-induced cough than dextromethorphan alone. Also, dextromethorphan and salbutamol were more effective in treating acute transient cough than dextromethorphan alone. In order to provide both antitussive and bronchodilator treatment, both drugs must be used. It would be desirable to provide a single cough suppressant providing antitussive and bronchodilator properties for treatment of a nonproductive cough.

Further, dextromethorphan is addictive and has severe side effects, including nausea, drowsiness, dizziness, hallucinations, vomiting, blurred vision, sweating, dilated pupils, hypertension and shallow respiration. Dextromethorphan is commonly abused as a recreational drug. Salbutamol also has severe side effects, including tremor, nervousness, headache, muscle cramps, dry mouth and palpitation. It would be desirable to provide an alternative for both drugs.

Although a comprehensive program of medical treatment would involve efforts to identify the underlying cause for nonproductive coughing and tailoring a treatment program towards the underlying cause, nevertheless, in many cases nonproductive coughing is a symptom that causes the patient discomfort, distress (either physical or social from an inability to suppress coughing when desired), an inability to sleep comfortably with resulting fatigue, and the like, so that often the patient desires at least temporary relief from the symptom, regardless of the underlying cause. Of course, it is generally not desirable to suppress a productive cough, but an antitussive, or an antitussive in combination with a bronchodilator when the cough is accompanied by bronchoconstriction, is useful for temporary symptomatic treatment or relief from a nonproductive cough. Thus, antitussive and bronchodilator use for an enaminone ester solving the aforementioned problems is desired.

SUMMARY OF THE INVENTION

The antitussive and bronchodilator use for an enaminone ester relates to the use of ethyl 4-[(4-chlorophenyl)amino]-6-methyl-2-oxocyclohex-3-en-1-oate (also referred to as "enaminone E121") for treatment of respiratory conditions, and particularly to the use of the ester as the active ingredient in a cough suppressant for nonproductive cough. The ester may be used to achieve an antitussive effect, a bronchodilator effect, or both in a patient in need thereof. The ester may be formulated in any desired delivery form (such as a tablet, a capsule, a time-release capsule, a syrup, a liquid, an injection, a spray, or an inhalant), and be combined with any suitable pharmaceutical carrier, vehicles, binders, fillers, disintegrators, lubricants, solubilizers, emulsifiers, surfactants, and other excipients.

By way of example, a dosage of at least 100 milligrams per kilogram of body weight is typically sufficient to achieve an antitussive or bronchodilatory effect in a patient when delivered by injection, or as a systemic dosage. When inhaled, a dosage of about 100 micrograms is sufficient for therapeutic effect.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The antitussive and bronchodilator use for an enaminone ester relates to respiratory treatments, and particularly to a cough suppressant for suppressing or inhibiting nonproductive cough symptomatic of a number of respiratory conditions with a therapeutically effective dose of ethyl 4-[(4-chlorophenyl)amino]-6-methyl-2-oxocyclohex-3-en-1-oate (also referred to as "enaminone E121"), or pharmaceutically acceptable salts thereof (it is anticipated that E121 ester salts should produce the same pharmaceutical effect as the pure ester). The ester is used to achieve an antitussive effect, and may also be used to achieve a bronchodilatory effect. As used herein, the term "antitussive effect" means relieving, preventing, inhibiting, and reducing the frequency or severity of cough, at least temporarily. As used herein, the term "bronchodilatory effect" means the relief of bronchoconstriction (particularly bronchoconstriction accompanying nonproductive cough), dilating or expanding the lumina of air passages of the lungs, reducing the incidence or severity of bronchoconstriction, or rendering air passages more patent, at least temporarily.

The therapeutically effective dose of ethyl 4-[(4-chlorophenyl)amino]-6-methyl-2-oxocyclohex-3-en-1-oate is delivered to the patient as either an inhalant, as an injection or in an ingestible form, preferably at dosages of at least 100 mg per kg of patient mass when delivered systemically or as an injection, or approximately 100 micrograms when delivered as an inhalant. As will be shown below, the inventors have experimentally found enaminone ester E121 to exhibit significant antitussive and bronchodilatory actions. As described below, experiments were carried out by inducing coughs in guinea pigs using citric acid, and treating one group of guinea pigs with 100 mg/kg enaminone ester E121, and comparing the results from this group against a control group.

The enaminone ester E121 is found to have direct airway smooth muscle (ASM) relaxant effects. Additionally, the ASM relaxant effects of enaminone ester E121 are found to show lower levels of tachyphalaxis than salbutamol (albuterol), a commonly used bronchodilator. The combined antitussive and bronchodilatory effects of enaminone ester E121 allow the compound to be used as an effective treatment for some types of coughs, as well as coughs associated with airway flow obstructions, providing at least temporary symptomatic relief, regardless of the underlying respiratory or pathological condition producing the cough.

Figure 1:
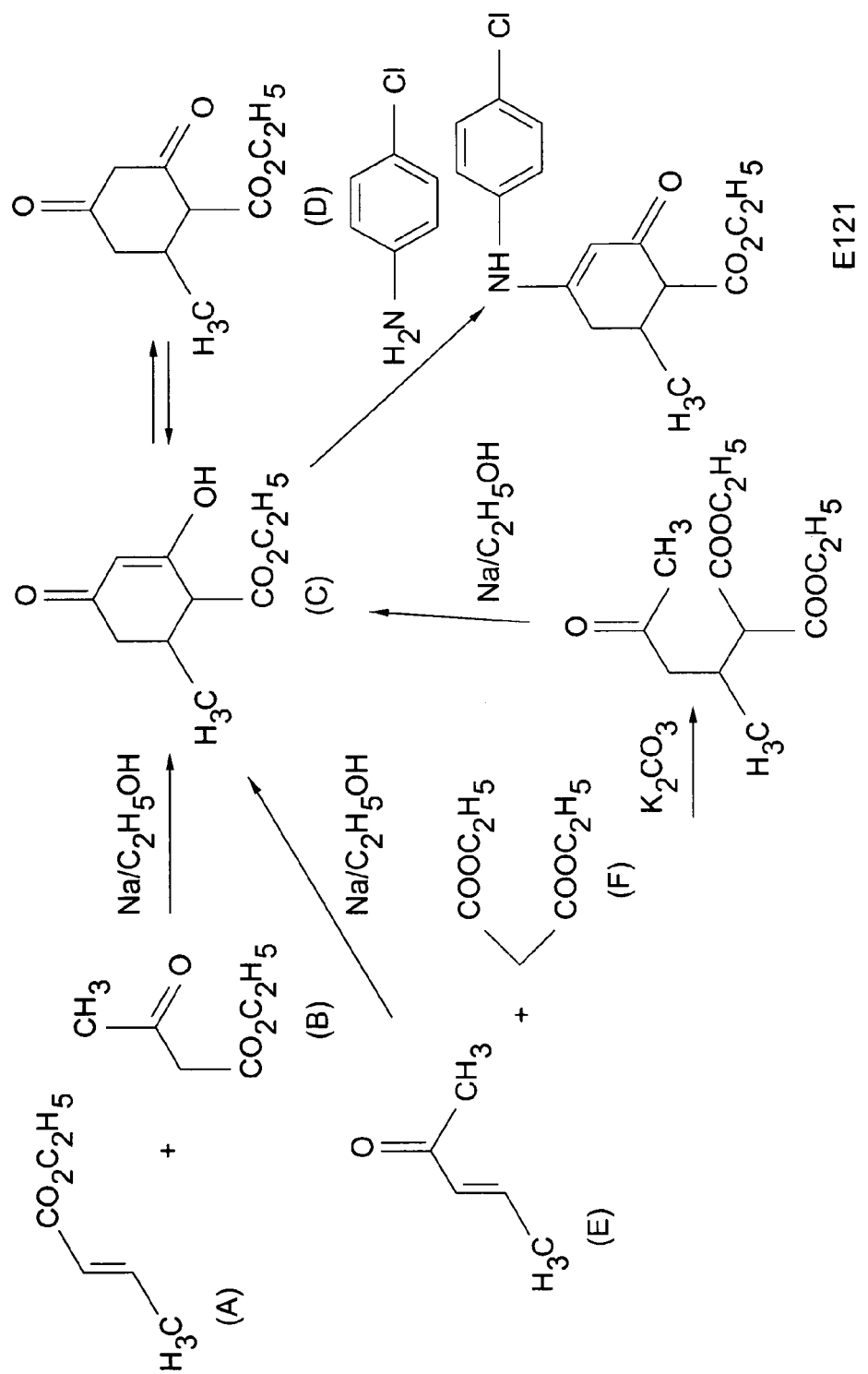
FIG. 1 illustrates chemical reactions for synthesizing ethyl 4-[(4-chlorophenyl)amino]-6-methyl-2-oxocyclohex-3-en-1-oate.

Ethyl 4-[(4-chlorophenyl)amino]-6-methyl-2-oxocyclohex-3-en-1-oate may be synthesized in several different ways. For example, FIG. 1 illustrates the cyclization reaction between ethyl crotonate (A) and ethyl acetoacetate (B) in the presence of freshly prepared sodium ethoxide, which forms an intermediate beta-hydroxy keto ester (C), which exists as two tautomers (C) and (D). Condensation of the intermediate beta-hydroxy keto ester (C) with 4-chloroaniline yields the enaminone ester E121. Alternatively, pent-2-en-4-one (E) may be reacted with diethyl malonate (F) in freshly prepared sodium ethoxide to form the intermediate beta-hydroxy keto ester (C). Another alternative route involves the reaction of (E) and (F) under mild conditions with potassium carbonate to form the adduct (G), which is cyclized in freshly prepared sodium ethoxide to form the intermediate beta-hydroxy keto ester (C). Thus, the synthesis of the intermediate beta-hydroxy keto ester (C) is unequivocal, and condensation with 4-chloroaniline yields enaminone E121.

The compound enaminone E121 is a cyclohexenone derivative. E121 is a stable solid at room temperature, and has a melting point of approximately between 161° and 163° C. when re-crystallized from ethyl acetate. The compound shows characteristic ultraviolet and infrared absorptions, and has a molecular formula of $C_{16}H_{18}NO_3Cl$, with a molecular weight of 307.5. Further, enaminone E121 has a calculated log P(C log P) value of 3.35. The proton nuclear magnetic resonance peaks of enaminone E121 in deuterated chloroform ($CDCl_3$) gives chemical shifts ($\delta$ ppm) of 1.06 (d, J=6.25 Hz, 3H) for the methyl group, 1.26 (t, J=6.90 Hz, 3H) for the methyl group of ethyl ester, 1.90-2.70 (m, 3H) for the cycloalkene ring, 3.10 (d, J=11.03 Hz, 1H) for the cycloalkene ring, 4.19 (q, J=6.90 Hz, 2H) for the methylene group of ethyl ester, 5.43 (s, 1H) for the vinyl proton, 7.51 (s, 1H) for NH, and 7.01-7.32 (m, 4H) for the phenyl ring.

Example 1

In order to test the effectiveness of enaminone ester E121 as an antitussive, two groups of guinea pigs were established. Group 1 was a control group, which consisted of ten guinea pigs, who were administered vehicle only (100% dimethyl sulfoxide [DMSO]) intraperitoneally. Group 2 was a test group, which consisted of ten guinea pigs, who were administered enaminone E121 (100 mg/kg in DMSO) intraperitoneally (i.e., via intraperitoneal injection). Each group was separately placed in a transparent whole body plythesmography box (Buxco, Troy, N.Y.) for testing one hour after administration of the vehicle or the enaminone ester E121, respectively.

Each group was allowed a settling period in the whole body plethysmograph, after which baseline airway function was recorded for 2 minutes before administration of an aerosol. Animals in each group were then exposed to citric acid (0.6 M) aerosol for 10 minutes, during which cough and airway function were recorded, and for an additional 5 minutes thereafter (a total of 15 minutes). The aerosols were generated using a DeVilbiss aerogen ultrasonic nebulizer (DeVilbiss, Somerset, Pa.), the nebulized spray having an aerodynamic mass median diameter droplet size range of 105 μm (manufacturer's indication). Assessment of cough and assessment of airway obstruction (Penh) were performed simultaneously.

Coughs were recorded from conscious, unrestrained guinea pigs manually by a trained observer as confirmation. The plethysmograph chamber was fitted with a microphone, which was connected to an external speaker allowing amplification of the cough sound. Coughs were recognized by the characteristic animal posture and a rapid, transient increase in airflow (approximately one hundred-fold) over and above the normal flow. Also, the criteria for cough included a "high sound" with the mouth open and a defined pattern in the sound signal, which distinguishes coughs from sneezes.

Figure 2:
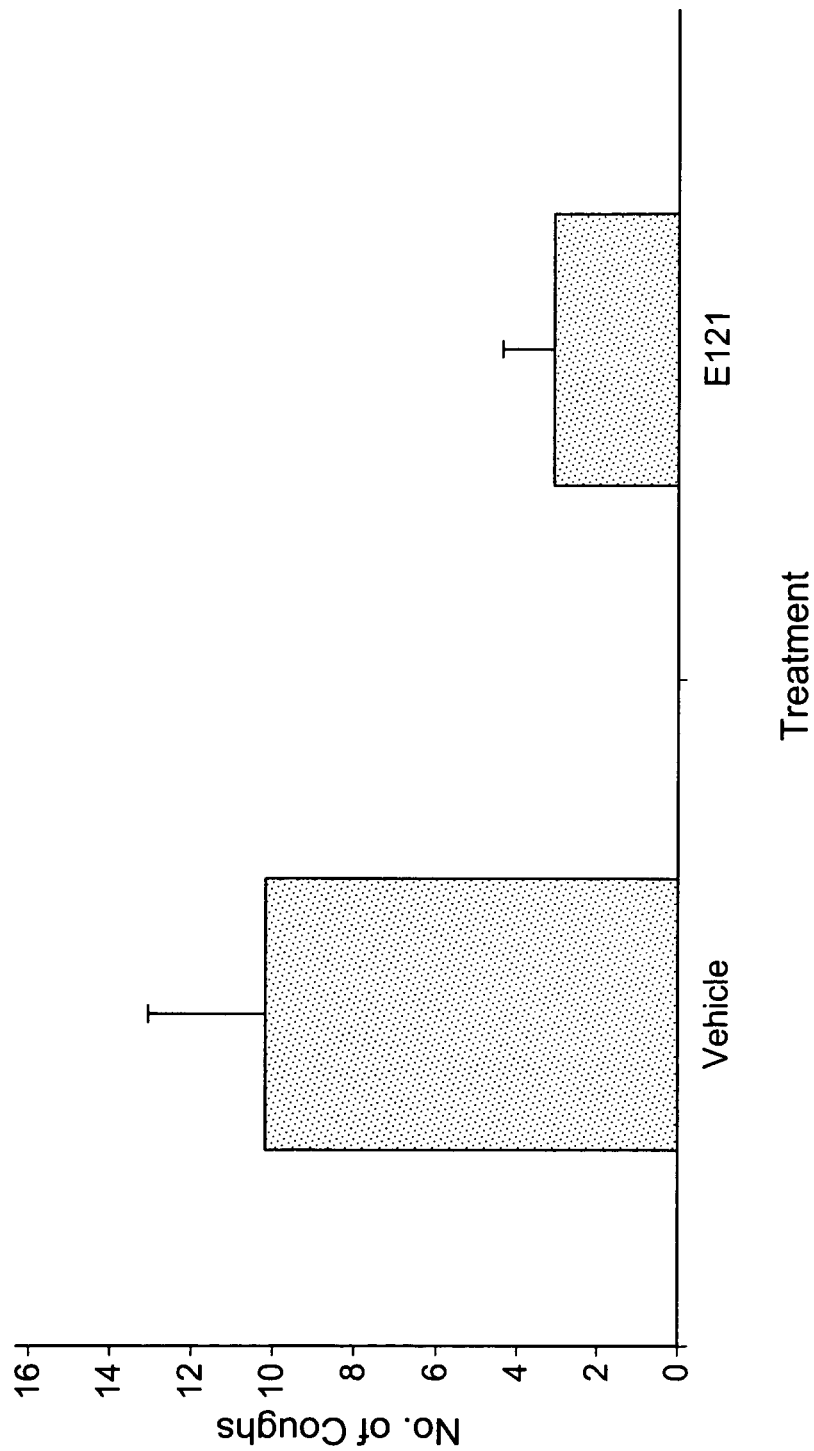
FIG. 2 is a comparison chart illustrating number of coughs counted between a vehicle, or control, group of guinea pigs and a group of guinea pigs treated with ethyl 4-[(4-chlorophenyl)amino]-6-methyl-2-oxocyclohex-3-en-1-oate).

FIG. 2 illustrates the number of coughs counted for the vehicle, or control group, vs. the group treated with enaminone ester E121. Each group included 10 guinea pigs. As shown graphically in FIG. 2, Group 2, which was administered enaminone E121, exhibited a substantially lower incidence of coughs than Group I, which was administered vehicle only, showing that enaminone E121, or ethyl 4-[(4-chlorophenyl)amino]-6-methyl-2-oxocyclohex-3-en-1-oate, produces an antitussive effect.

Simultaneous with the testing for cough, both groups were tested for airway obstruction. A pneumotachograph with defined resistance in the wall of the main chamber acted as a low-pass filter and allowed for thermal compensation. The chamber was fitted with a microphone and connected to both an external speaker and a computer to allow visualization of the sound signal. The plethysmograph was also connected to a bias flow regulator that was supplying air at a rate of 3 L/min and withdrawing air at a rate of 4 L/min, the difference being taken up by airflow into the box through the pneumotachograph.

The pressure differences between the main chamber of the whole body plethysmograph containing the animals and a reference chamber (box pressure signal) were measured. Depending upon these box pressure signals, the phases of the respiratory cycle, peak inspiratory pressure (PIP), peak expiratory pressure (PEP), and tidal volumes, and an index of airway caliber, the enhanced pause (Penh), was calculated as Penh=Pause×(PEP/PIP).

Penh is a dimensionless value that reflects changes in the waveform of the box pressure signal from inspiration and expiration (PIP, PEP) and combines it with the timing comparison of early and late expiration (Pause). These measurements and calculations were performed at the same time that the coughs were being counted. The lower the Penh, the lower the degree of bronchoconstriction.

Figure 3:
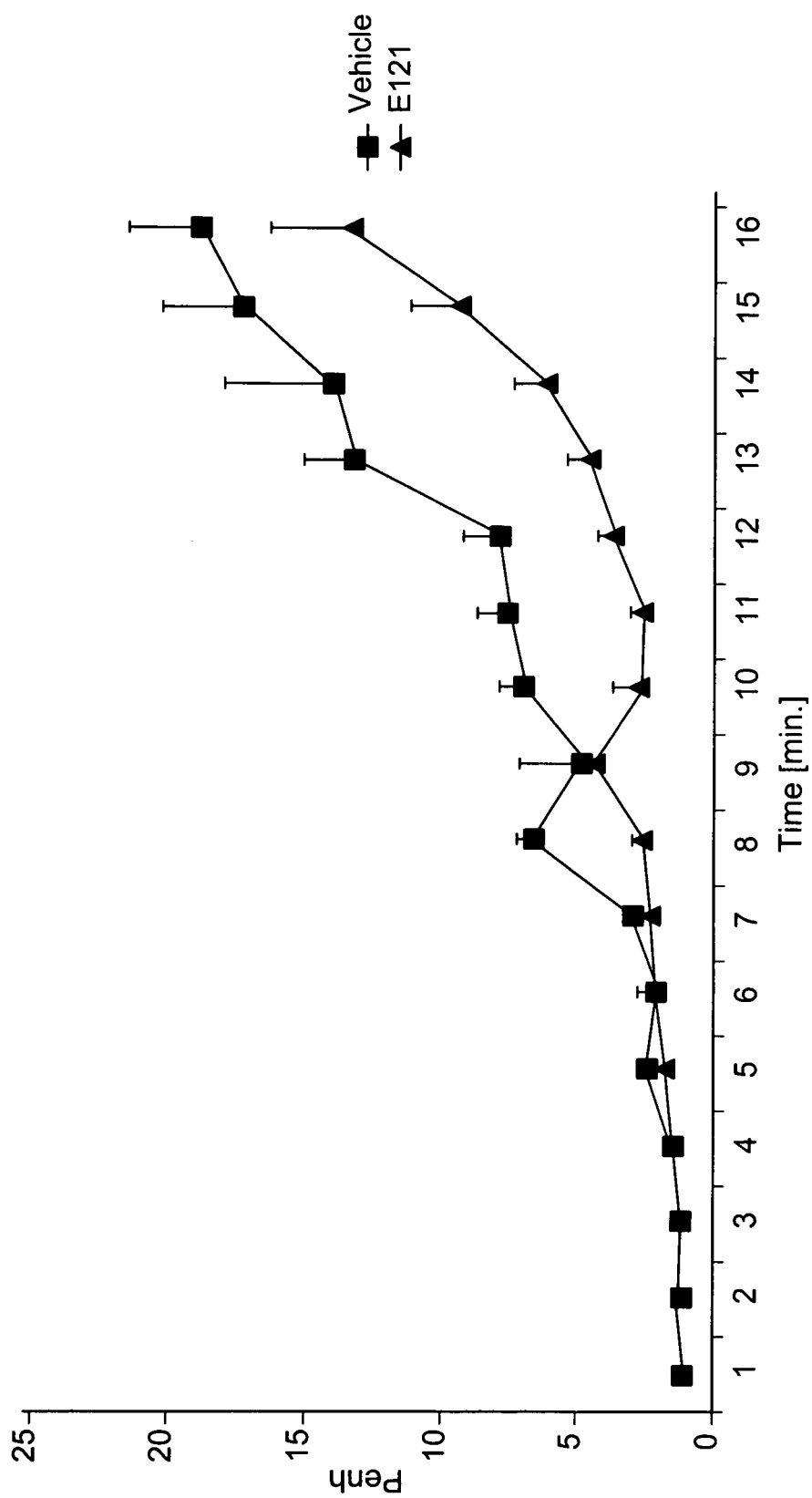
FIG. 3 is a comparison graph showing enhanced pause (Penh) as a function of time for the two groups of FIG. 2.

FIG. 3 illustrates the enhanced pause (Penh) counted for both groups as a function of time, with treatment beginning at time zero minutes. As shown in FIG. 3, Group 2, which was administered enaminone ester E121, experienced less bronchoconstriction or airway obstruction than Group 1, which received vehicle only, demonstrating that enaminone ester E121, or ethyl 4-[(4-chlorophenyl)amino]-6-methyl-2-oxocyclohex-3-en-1-oate, produces a bronchoprotective effect.

Example 2

In order to further demonstrate the effect of ethyl 4-[(4-chlorophenyl)amino]-6-methyl-2-oxocyclohex-3-en-1-oate on air passages, agonist-induced relaxation was studied on guinea pig bronchial preparations pre-contracted with carbachol (3 μM), as follows.

Two groups of guinea pigs, each group containing twelve guinea pigs, were decapitated under light ether anesthesia and the tracheas were dissected out with the lungs en bloc. The origin of bifurcation of the trachea into bronchioles was identified after removal of the excess connective tissue. The isolated bronchioles were cut into ring segments of 4 mm in length. The preparations were mounted in organ baths containing 25 mL Krebs-Henseleit (KH) solution at pH 7.4, maintained at 37° C. and aerated with a 95% $O_2$ and 5% $CO_2$ mixture. The preparations were left to stabilize for 45 minutes, changing the KH solution at 15-minute intervals. A pre-tension of 0.75 gm was applied, and a stabilization period of 45 minutes was allowed until a stable baseline tone was obtained. Isolated segments of the bronchioles were pre-contracted with carbachol (3 μM). Responses of the carbachol pre-contracted bronchial ring segments to the different agonists were determined by measurement of changes in the isometric tension, using computerized automatic organ bath analyzing instruments.

Bronchodilator responses to salbutamol ($10^{-9}$-$3 \times 10^{-4}$ M) and enaminone ester E121 ($10^{-9}$-$10^{-4}$ M) were investigated on different preparations of the bronchioles. After obtaining a steady level of pre-contraction, cumulative concentration response curves (CRC) were established for salbutamol ($10^{-9}$-$3 \times 10^{-4}$ M) and enaminone ester E121 ($10^{-9}$-$10^{-4}$ M). The response to each concentration of the agonist was left to stabilize before adding the next drug concentration. The bronchodilator responses were expressed as a percentage reduction of the carbachol induced pre-contraction. To assess whether there was a tachyphylaxis to enaminone E121 or to salbutamol, the CRCs for both agonists were repeated after one hour.

Figure 4:
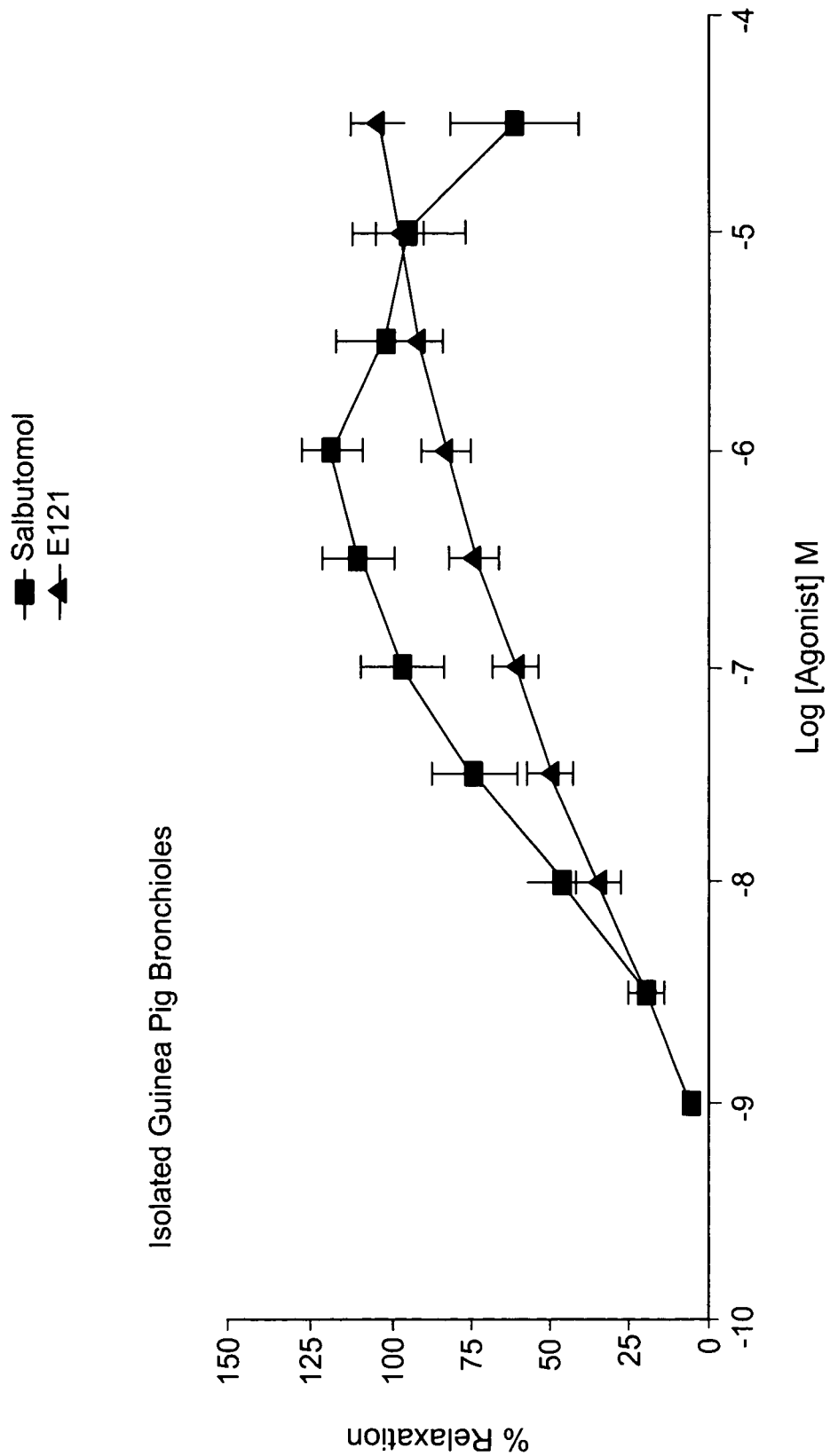
FIG. 4 is a logarithmic comparison graph showing relaxation responses as a function of agonist concentration for the two groups of FIG. 2.

After the carbachol-induced contractions were stabilized, ascending concentrations of the agonists, salbutamol ($1 \times 10^{-9}$-$3 \times 10^{-4}$ M), or the enaminone ester E121 ($1 \times 10^{-9}$-$1 \times 10^{-4}$ M) were added cumulatively to the organ baths to establish cumulative concentration-response curves. Inhibitory responses of the agonists were expressed as a percentage reduction of carbachol-induced tone. The results for the two groups are shown in FIG. 4, expressed as percentage of relaxation vs. logarithm of the agonist concentration. As shown in FIG. 4, the bronchiole segments bathed in enaminone ester E121 experienced similar relaxation to those bathed in salbutamol (albuterol), further reinforcing the conclusion that enaminone E121, or ethyl 4-[(4-chlorophenyl)amino]-6-methyl-2-oxocyclohex-3-en-1-oate, produces a bronchodilatory effect.

It should be understood that the patient may be dosed with enaminone ester E121 via inhalation, ingestion, in the form of a sub-dermal patch, via injection or through any other suitable type of delivery.

It is to be understood that the present invention is not limited to the embodiment described above, but encompasses any and all embodiments within the scope of the following claims.

We claim:

1. A method of generating a bronchodilatory effect in a patient in need thereof, comprising the step of administering to the patient an effective amount of ethyl 4-[(4-chlorophenyl)amino]-6-methyl-2-oxocyclohex-3-en-1-oate or a pharmaceutically acceptable salt thereof.

2. The method of generating a bronchodilatory effect according to claim 1, wherein said administering step further comprises administering the ethyl 4-[(4-chlorophenyl)amino]-6-methyl-2-oxocyclohex-3-en-1-oate or pharmaceutically acceptable salt thereof to the patient via injection.

3. The method of generating a bronchodilatory effect according to claim 1, wherein the ethyl 4-[(4-chlorophenyl)amino]-6-methyl-2-oxocyclohex-3-en-1-oate or a pharmaceutically acceptable salt thereof is formulated as a tablet for oral ingestion.

4. The method of generating a bronchodilatory effect according to claim 1, wherein the ethyl 4-[(4-chlorophenyl)amino]-6-methyl-2-oxocyclohex-3-en-1-oate or a pharmaceutically acceptable salt thereof is formulated as a capsule for oral ingestion.

5. The method of generating a bronchodilatory effect according to claim 1, wherein the ethyl 4-[(4-chloropheny)amino]-6-methyl-2-oxocyclohex-3-en-1-oate or a pharmaceutically acceptable salt thereof is formulated as a syrup for oral ingestion.

6. The method of generating a bronchodilatory effect according to claim 1, wherein the ethyl 4-[(4-chlorophenyl)amino]-6-methyl-2-oxocyclohex-3-en-1-oate or a pharmaceutically acceptable salt thereof is formulated as a liquid for oral ingestion.

7. The method of generating a bronchodilatory effect according to claim 1, wherein the ethyl 4-[(4-chlorophenyl)amino]-6-methyl-2-oxocyclohex-3-en-1-oate or a pharmaceutically acceptable salt thereof is formulated for administration by inhalation.

8. The method of generating a bronchodilatory effect according to claim 1, wherein said administering step further comprises administering an effective amount of ethyl 4-[(4-chlorophenyl)amino]-6-methyl-2-oxocyclohex-3-en-1-oate or a pharmaceutically acceptable salt thereof, the effective amount being at least 100 mg of ethyl 4-[(4-chlorophenyl)amino]-6-methyl-2-oxocyclohex-3-en-1-oate per kilogram of the patient's body weight.

9. The method of generating a bronchodilatory effect according to claim 1, wherein said administering step further comprises the step of administering to the patient an effective antitussive amount of ethyl 4-[(4-chlorophenyl)amino]-6-methyl-2-oxocyclohex-3-en-1-oate or a pharmaceutically acceptable salt thereof.

10. The method of generating a bronchodilatory effect according to claim 1, wherein said administering step further comprises administering an effective amount of ethyl 4-[(4-chlorophenyl)amino]-6-methyl-2-oxocyclohex-3-en-1-oate or a pharmaceutically acceptable salt thereof as an inhalant, the effective cough suppressing amount being about 100 micrograms of ethyl 4-[(4-chlorophenyl)amino]-6-methyl-2-oxocyclohex-3-en-1-oate.

11. A method of achieving an effect in a patient, comprising the step of administering to the patient an effective amount of ethyl 4-[(4-chlorophenyl)amino]-6-methyl-2-oxocyclohex-3-en-1-oate or a pharmaceutically acceptable salt thereof, wherein the effect is bronchodilation.

12. The method of achieving an effect in a patient according to claim 11, wherein said administering step further comprises administering the ethyl 4-[(4-chlorophenyl)amino]-6-methyl-2-oxocyclohex-3-en-1-oate or pharmaceutically acceptable salt thereof to the patient via injection.

13. The method of achieving an effect in a patient according to claim 12, wherein the effective amount administered to the patient via injection is at least 100 mg of ethyl 4-[(4-chlorophenyl)amino]-6-methyl-2-oxocyclohex-3-en-1-oate per kilogram of the patient's body weight.

14. The method of achieving an effect in a patient according to claim 11, wherein said administering step further comprises administering the ethyl 4-[(4-chlorophenyl)amino]-6-methyl-2-oxocyclohex-3-en-1-oate or pharmaceutically acceptable salt thereof to the patient by inhalation.

* * * * *